US00PP14690P29

(12) United States Plant Patent
Ramirez

(10) Patent No.: US PP14,690 P2
(45) Date of Patent: Apr. 13, 2004

(54) IMPATIENS PLANT NAMED 'BALFAFORG'

(50) Latin Name: *Impatiens hybrida*
Varietal Denomination: Balfaforg

(75) Inventor: Rolando Solano Ramirez, Dulce Numbre de Cartago (CR)

(73) Assignee: Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/359,748

(22) Filed: Feb. 6, 2003

(51) Int. Cl.[7] ..... A01H 5/00
(52) U.S. Cl. ..... Plt./317
(58) Field of Search ..... Plt./317

*Primary Examiner*—Bruce R. Campell
*Assistant Examiner*—June Hwu
(74) *Attorney, Agent, or Firm*—C. A. Whealy

(57) ABSTRACT

A new and distinct cultivar of Impatiens plant named 'Balfaforg', characterized by its upright, outwardly spreading and mounded plant habit; large orange-colored flowers that are positioned above and beyond the leaves; freely flowering habit; and dark green-colored leaves.

1 Drawing Sheet

Botanical classification/cultivar designation: *Impatiens hybrida* cultivar Balfaforg.

BACKGROUND OF THE INVENTION

The present Invention relates to a new and distinct cultivar of Impatiens plant, botanically known as *Impatiens hybrida,* and hereinafter referred to by the name 'Balfaforg'.

The new Impatiens is a product of a planned breeding program conducted by the Inventor in Cartago, Costa Rica. The objective of the breeding program was to develop new Impatiens cultivars with upright to trailing growth habit, freely branching habit and large flower size.

The new Impatiens originated from a cross-pollination made by the Inventor in 2000, of a proprietary *Impatiens hybrida* selection identified as code number N1649-2, not patented, as the female, or seed parent, with an unidentified selection of *Impatiens flaccida*, not patented, as the male, or pollen parent. The cultivar Balfaforg was discovered and selected by the Inventor as a flowering plant within the progeny of the stated cross-pollination in a controlled environment in Cartago, Costa Rica.

Asexual reproduction of the new cultivar by terminal cuttings taken at Cartago, Costa Rica since August, 2000, has shown that the unique features of this new Impatiens are stable and reproduced true to type in successive generations of asexual reproduction.

SUMMARY OF THE INVENTION

The following traits have been repeatedly observed and are determined to be the unique characteristics of 'Balfaforg'. These characteristics in combination distinguish 'Balfaforg' as a new and distinct Impatiens cultivar:

1. Upright, outwardly spreading and mounded plant habit.
2. Freely branching growth habit.
3. Dark green-colored leaves.
4. Large orange-colored flowers that are positioned above and beyond the foliage.
5. Freely flowering habit.

Plants of the new Impatiens differ primarily from plants of the parent selections in plant habit and flower color.

The new Impatiens can be compared to the *Impatiens hybrida* cultivar Balfaflav, not patented. However, in side-by-side comparisons conducted in West Chicago, Ill., plants of the new Impatiens differed from plants of the cultivar Balfaflav in the following characteristics:

1. Plants of the new Impatiens were shorter and had shorter internodes than plants of the cultivar Balfaflav.
2. Plants of the new Impatiens had longer petioles than plants of the cultivar Balfaflav.
3. Plants of the new Impatiens had larger flowers than plants of the cultivar Balfaflav.

The new Impatiens can also be compared to the *Impatiens hybrida* cultivar Balfaflila, not patented. However, in side-by-side comparisons conducted in West Chicago, Ill., plants of the new Impatiens differed from plants of the cultivar Balfaflila in the following characteristics:

1. Plants of the new Impatiens were shorter but broader than plants of the cultivar Balfaflila.
2. Plants of the new Impatiens were more freely branching than plants of the cultivar Balfaflila.
3. Plants of the new Impatiens had longer petioles than plants of the cultivar Balfaflila.
4. Plants of the new Impatiens had larger flowers than plants of the cultivar Balfaflila.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Impatiens.

The photograph at the top of the sheet comprises a side perspective view of a flowering plant of 'Balfaforg'.

The photograph at the bottom of the sheet is close-up view of a typical flower and leaves of 'Balfaforg'.

DETAILED BOTANICAL DESCRIPTION

The cultivar Balfaforg has not been observed under all possible environmental conditions. The phenotype may vary somewhat with variations in environment such as temperature and light intensity without, however, any variance in genotype. The aforementioned photographs and following observations and measurements describe plants grown in West Chicago, Ill., under commercial practice in a polycarbonate-covered greenhouse with day temperatures ranging from 20 to 24° C., night temperatures ranging from 14 to 20° C. and light levels ranging from 4,000 to 7,000 footcandles. Rooted young plants were planted in 10-cm containers and had been growing for about 14 weeks when the photographs and the description were taken.

In the following description, color references are made to The Royal Horticultural Society Colour Chart, 2001 Edition, except where general terms of ordinary dictionary significance are used.

Botanical classification: *Impatiens hybrida* cultivar Balfaforg.

Parentage:

*Female parent.*—Proprietary *Impatiens hybrida* selection identified as code number N1649-2, not patented.

*Male parent.*—Unidentified *Impatiens flaccida* selection, not patented.

Propagation:

*Type cutting.*—Terminal cuttings.

*Time to initiate roots.*—About 7 days at 18° C.

*Time to produce a rooted young plant.*—About 21 days at 18° C.

*Root description.*—Fibrous.

*Rooting habit.*—Freely branching.

Plant description:

*General appearance.*—Upright, outwardly spreading and mounded plant habit; freely basal branching growth habit, about six basal branches develop per plant. Moderately vigorous.

*Plant height.*—About 15.6 cm.

*Plant diameter or spread.*—About 43.2 cm.

*Lateral branches.*—Length: About 16 cm. Diameter: About 7 mm. Internode length: About 2.5 cm. Color: 143C overlain with 183C.

*Foliage description.*—Arrangement: Opposite or in whorls of three to five. Length: About 5.4 cm. Width: About 2.6 cm. Shape: Elliptic. Apex: Acuminate. Base: Attenuate. Margin: Serrulate with ciliation. Texture, upper and lower surfaces: Smooth, glabrous. Venation pattern: Pinnate. Color: Young foliage, upper surface: Darker than N134A. Young foliage, lower surface: 146A. Fully expanded foliage, upper surface: Darker than 139A. Fully expanded foliage, lower surface: 137C. Venation, upper and lower surfaces: 143A. Petiole: Length: About 1.2 cm. Diameter: About 2 mm. Texture, upper and lower surfaces: Smooth, glabrous. Color, upper and lower surfaces: 145B overlain with 183C.

Flower description:

*Flower type and flowering habit.*—Single large flowers. Freely flowering, usually about ten flowers and flower buds per lateral branch. Flowers positioned above and beyond the foliage and typically face upward or outward. Flowers not fragrant. Petals self-cleaning; gynoecium persistent.

*Flower longevity.*—Flowers last about one week on the plant.

*Natural flowering season.*—Flowering continuous from spring until fall in West Chicago, Ill.

*Flower buds.*—Length: About 2 cm. Diameter: About 1.1 cm. Shape: Ovoid. Color: 40C.

*Flower diameter.*—About 6 by 5.6 cm.

*Flower depth.*—About 1.1 cm.

*Flower shape.*—Rounded to slightly cupped.

*Petals.*—Quantity: Five per flower, imbricate. Length, banner petal: About 2.5 cm. Length, lateral petals: About 3.1 cm. Length, basal petals: About 3.7 cm. Width, banner petals: About 3.6 cm. Width, lateral petals: About 2.6 cm. Width, basal petals: About 3.2 cm. Shape: Obovate. Apex: Emarginate. Base, banner petal: Truncate. Base, lateral and basal petals: Attenuate. Margin: Entire. Texture, upper and lower surfaces: Smooth, glabrous. Color: When opening, upper surface: N30B. When opening, lower surface: Slightly lighter than 33C. Fully opened, upper surface: N30B; towards the base, 59B to 59D; color becoming closer to N30A with development. Fully opened, lower surface: Slightly lighter than 33C.

*Spur.*—Quantity: One per flower. Length: About 6.2 cm. Aspect: Curved. Color: 145B.

*Peduncles.*—Length: About 5.5 cm. Diameter: About 1 mm. Strength: Strong; flexible. Angle: Acute. Color: 145A faintly overlain with 183C.

*Reproductive organs.*—Androecium: Stamen quantity/arrangement: Five fused at anthers, hooded; filaments free. Anther length: About 2 mm. Anther shape: Obovate. Anther color: 63D. Pollen amount: Abundant. Pollen color: 13D. Gynoecium: Pistil quantity: One per flower. Pistil length: About 4 mm. Stigma length: Less than 1 mm. Stigma color: Colorless. Style length: Less than 1 mm. Style color: 145A. Ovary arrangement: Five-celled. Ovary length: About 3 mm. Ovary texture: Smooth. Ovary color: 143B.

*Seeds/fruits.*—Seed and fruit development has not been observed.

Disease/pest resistance: Plants of the new Impatiens have not been observed to be resistant to pathogens and pests common to Impatiens.

It is claimed:

1. A new and distinct cultivar of Impatiens plant named 'Balfaforg', as illustrated and described.

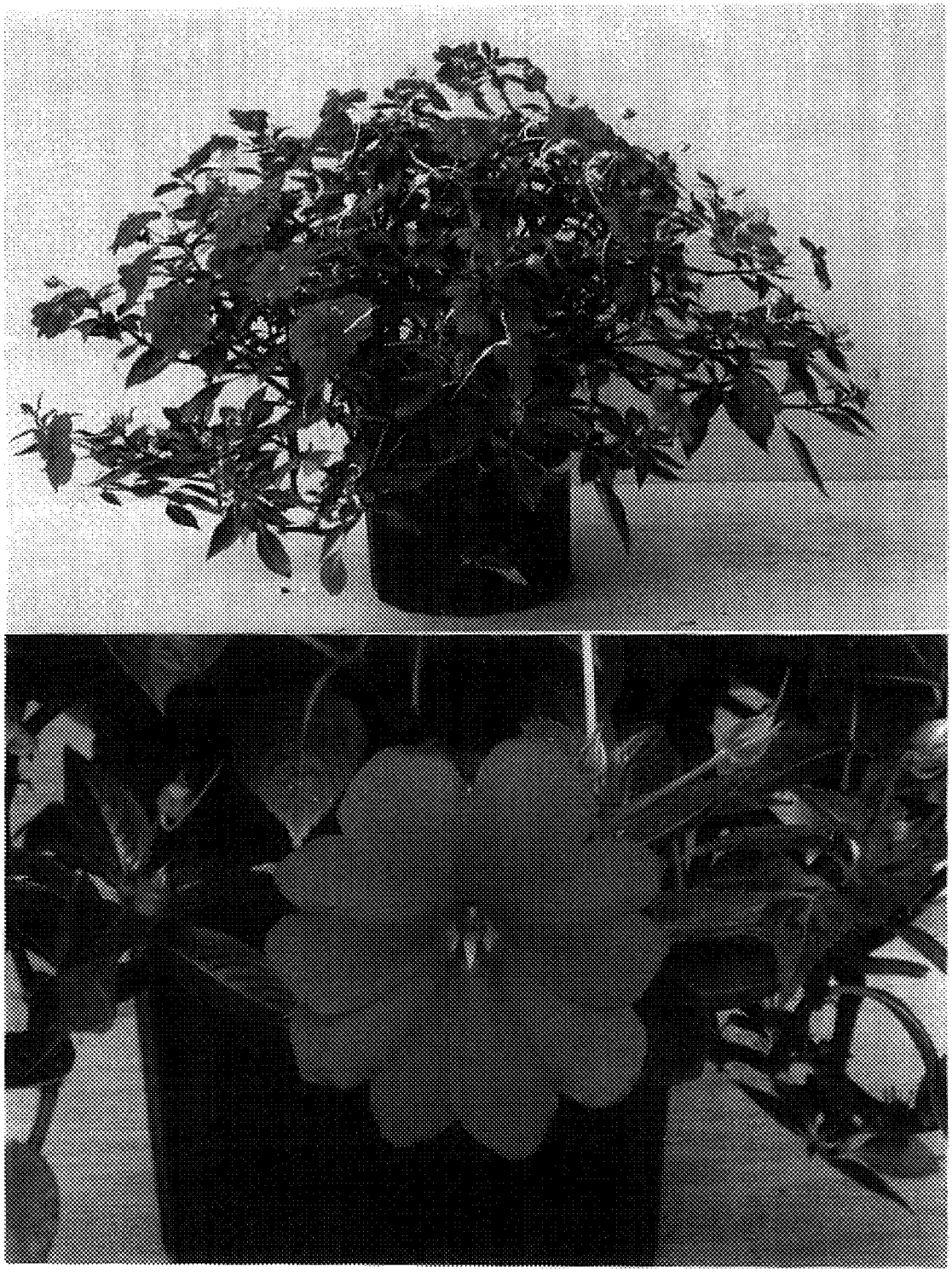

* * * * *